United States Patent [19]

Riquin

[11] Patent Number: 4,502,764

[45] Date of Patent: Mar. 5, 1985

[54] CONTACT LENS FOR THE OBSERVATION AND TREATMENT OF A POINT IN THE EYE

[75] Inventor: Didier Riquin, Tours, France

[73] Assignee: Lasag AG, Thun, Switzerland

[21] Appl. No.: 479,710

[22] Filed: Mar. 28, 1983

[30] Foreign Application Priority Data

Apr. 16, 1982 [CH] Switzerland ............... 2317/82

[51] Int. Cl.³ .................... A61B 3/00; G02C 7/04
[52] U.S. Cl. ................................. 351/160 R; 351/219
[58] Field of Search ............. 351/160 R, 160 H, 219

[56] References Cited

U.S. PATENT DOCUMENTS

| | | | |
|---|---|---|---|
| 3,467,099 | 9/1969 | Lotmar | 351/219 X |
| 3,726,587 | 4/1973 | Kendall | 351/161 |
| 4,067,646 | 1/1979 | Nohda | 351/219 |
| 4,134,647 | 1/1979 | Ramos-Caldera | 351/219 |

FOREIGN PATENT DOCUMENTS

| | | |
|---|---|---|
| 30210 | 6/1981 | European Pat. Off. |
| 2248814 | 5/1975 | France . |
| 2255616 | 7/1975 | France . |
| WO82/02656 | 8/1982 | PCT Int'l Appl. ......... 351/219 |

Primary Examiner—John K. Corbin
Assistant Examiner—Scott J. Sugarman
Attorney, Agent, or Firm—Peter L. Berger

[57] ABSTRACT

The contact lens (1) for observation and treatment by a coherent radiation beam of a working point T of the eye comprises, for example, an entry lens (4) coupled to a contact lens (5) designed to be applied to the cornea of the eye, the optic axes (6) of said lenses being merged. The entry surface of the lens is spherical and is associated with Weierstrass points A and A' and the image of point A' by the rest of the contact lens is merged with said working point T.

10 Claims, 4 Drawing Figures

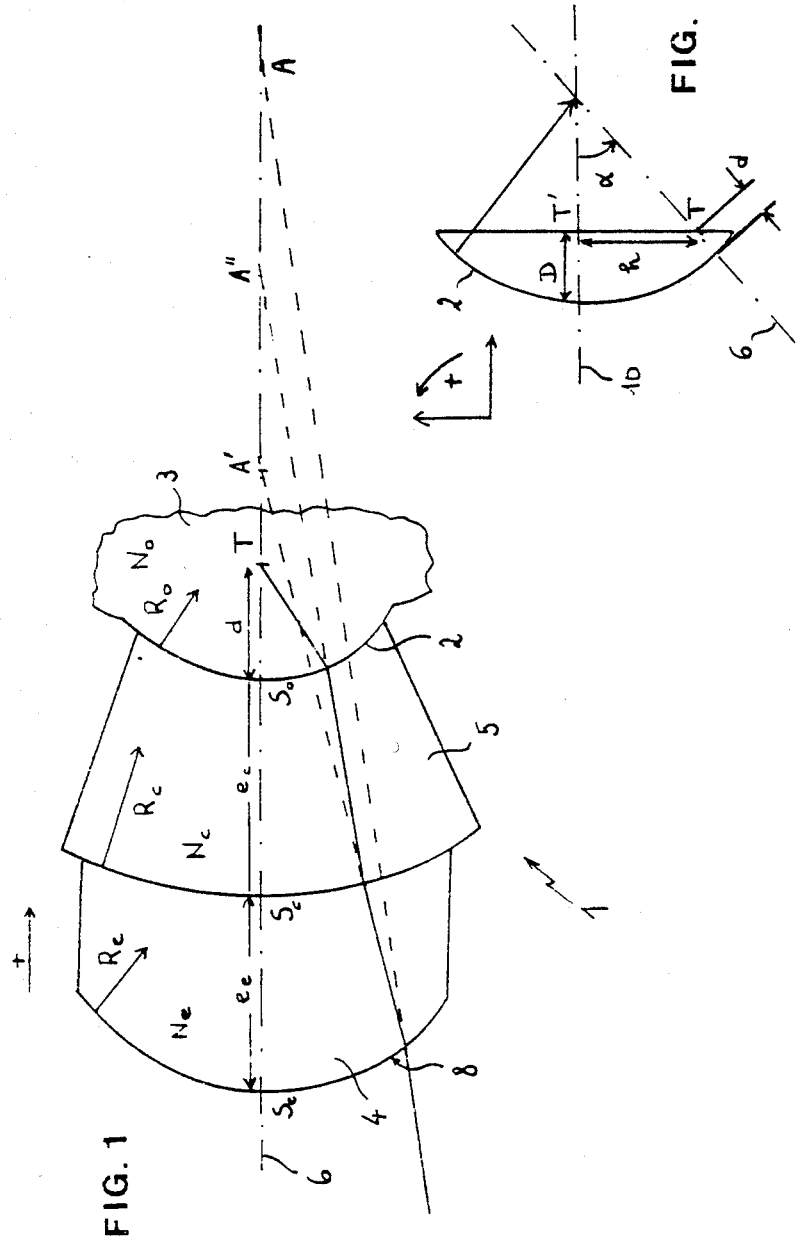

4,502,764

CONTACT LENS FOR THE OBSERVATION AND TREATMENT OF A POINT IN THE EYE

BACKGROUND OF THE INVENTION

This invention concerns a contact lens, particularly well suited for observation of the eye and its treatment by a coherent radiation optical beam.

Different eye diseases, like, for example, certain glaucomas, cataract or even disorders resulting from the presence of membranes can necessitate, for their operation or the preparation of that operation, the use of a laser beam of very high energy density in certain regions of the eye. For that purpose, ophthalmologic treatment units of the type described in the European patent application published under No. 0 030 210 in the assignee's name herein are used. Those units make it possible to direct a laser beam toward the eye consisting usually of very short but very high-intensity pulses delivered, for example, by an Nd-YAG laser operating on Q-Switch mode. The width of the beam exiting from the unit is in the order of 16°.

One can, of course, envisage directing that beam straight to the eye without using a contact lens, notably, in order to reach the iris or the vicinity of the crystalline surface by a firing in a direction parallel to the axis of the eye. The narrowness of the beam then guarantees slight width aberrations on entering the eye but also gives rise to numerous disadvantages. In particular, the risks of reaching zones other than the one really aimed at are increased, with the localization of the optical click phenomenon taken advantage of to treat this zone being less fine. The focusing spot of the beam on the target is also larger.

There are various contact lenses that can be used. Three shall be identified.

The Goldmann type lenses are made in one piece, usually of an organic material, e.g., acrylic, and they have a plane or very slightly spherical entry surface. Originally, they were provided essentially for examination of the fundus of the eye, but they are also used for interventions in the anterior chamber of the eye. Those contact lenses do not solve the problems associated with the width of the beam, but such lenses lessen the problems with respect to the previous solution. Furthermore, these lenses introduce marked aberrations at the entry face. Their essential advantage is to assure very good reliability and the patient's comfort at the contact lens-eye interface due to the very good surface state that can be obtained with the materials used. That surface state prevents the formation of microclicks at that interface. On the other hand, the addition to the entry surface of an anti-reflecting coating for the wavelengths of the treatment beam (1.06μ for the Nd-YAG laser) and in the visible range presents difficulties not yet mastered.

The Abraham type lenses consist of a mineral glass entry lens coupled eccentrically with a Goldmann type contact lens. Those lenses, usable for iridectomy alone, make it possible to widen the treatment beam, which enhances its better focusing. Furthermore, the entry face can be easily treated. However, added to the aberrations at the entry surface is a coma aberration in the eye entry diopter due to the conjugate effect of a greater width and an off-centering of the lens.

The Roussel type lenses more recently developed and described, for example, in European Patent Application No. 82 810 044.6 in the assignee's name herein are made in one piece of mineral glass and contain a mirror-forming side face. The spherical entry surface forms a wave surface for the incident beam, the width of which is not modified. The essential advantage of these lenses is to enable the aberrations to be considerably reduced because of their better geometry. They are, furthermore, not very sensitive to rotations of the lens. On the other hand, their use is relatively difficult due to the presence of the mirror. The inclination of the treatment beam in relation to the axis of the eye, furthermore, diminishes firing efficiency. Finally, by reason of the interface problems already explained above, they do not guarantee optimum reliability at the mineral glass-cornea junction.

SUMMARY OF THE INVENTION

That is why an object of this invention is to propose a new contact lens which exhibits excellent qualities in spite of the sometimes contradictory requirements to which these devices are subject. The structure of the contact lens is determined so as to widen the incident treatment beam, to limit aberrations to a minimum, to make possible firings as perpendicular to the tissue targeted as possible and to guarantee reliability and the convenience of the patient at the glass-cornea interface and of the physician at entry of the beam into the lens (anti-reflecting treatment), without demanding from the physician of an overly critical positioning of the lens on the cornea.

For that purpose, the contact lens of the invention designed for observation and treatment with a coherent radiation beam of a working point T (FIG. 1) of the eye contains at least one entry surface and one contact surface provided to be applied on the cornea of the eye, the optic centers being situated on the axis of the symmetry of the lens. In addition, the entry surface of the entry lens is spherical, and it is associated with Weierstrass points A and A', the image of point A' by the rest of the contact lens and the parts of the eye crossed by the beam being merged with said working point T.

The resultant advantage of the use of Weierstrass points is well known in optics, since aplanatically conjugate points are involved, operative for a magnification equal to the index of the material used for the entry lens (in the order of 1.5). The width aberrations on entry of the contact lens are eliminated by virtue of this mode of operation, and focusing of the beam is achievable. When using at least two coupled lenses, it is possible to utilize a mineral glass for the entry lens and an organic glass for the contact lens.

The invention will be clearly understood by reading the specification in conjunction with the attached drawings.

BRIEF DESCRIPTION OF THE DRAWINGS

FIGS. 1 and 2 are schematic representations making it possible to illustrate, in general, the conditions of operation and use of a contact lens according to the invention.

DETAILED DESCRIPTION

Figure 3:
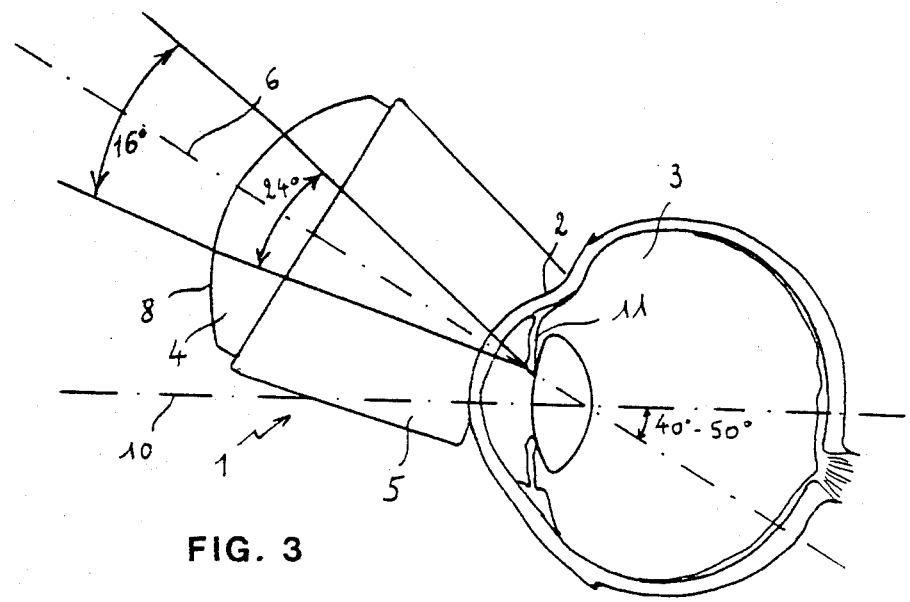
FIGS. 3 and 4 are sectional views of two contact lenses and of the eye to which they are applied according to two particular embodiments of the invention.

On FIG. 1, the contact lens, generally referenced as 1, applied to the cornea 2 of an eye 3, is represented in section and schematically. The contact lens 1 contains an entry lens 4 coupled to a contact lens 5, the contact surface of which is intended to be in contact with the cornea 2. The optic axes of lenses 4 and 5 are merged and designated by numeral 6. The intersections of single axis 6 with the air-entry lens, entry lens-contact lens and contact lens-eye diopters are respectively represented by points Se, Sc and So. The center thicknesses of entry lens 4 and contact lens 5 are respectively represented by magnitudes ec and ec. Also represented on axis 6 is working point T which is distance d from point So. In the explanations which follow, symbols Re, Rc and Ro, respectively, represent the radii of curvature of the air-entry lens, entry lens-contact lens and contact lens-eye diopters. Likewise, the indices of refraction of the entry lens, contact lens and eye are respectively designated by the symbols Ne, Nc and No.

According to the invention, the spherical entry surface 8 of the entry lens 4 is associated with Weierstrass points A and A', while the rest of the contact lens and the parts of the eye crossed by the beam bring the image of point A' to working point T. In particular, point A'' represents the image of point A' by the entry lens-contact lens diopter.

With the structure of FIG. 1, the following equations can then be written:

Weierstrass equations for the contact lens-eye diopter $$\frac{Nc}{x} = \frac{No}{d} + \frac{Nc - No}{Ro} \text{ with } x = SoA''$$

for the entry lens-contact lens diopter $$\frac{Ne}{ScA'} = \frac{Nc}{x + ec} + \frac{Ne - Nc}{Rc}$$

for the air-entry lens diopter $$SeA' = ScA' + e_e$$

$$SeA' = \frac{Ne + 1}{Ne} Re$$

$$SeA = (Ne + 1) Re$$

The combination of these equations then makes it possible to obtain the general equation linking the geometric and optical characteristics of the different lenses and of the eye for a contact lens according to FIG. 1.

$$Re \simeq \frac{Ne^2}{Ne + 1} \left( \frac{1}{\frac{Nc}{\frac{No}{d} + \frac{Nc - No}{Ro}} + ec} + \frac{Ne - Nc}{Rc} + \frac{ee}{Ne} \right)$$

The different magnitudes entering into the general equation can vary within the following limits:

| 7 mm | ≦ Ro | ≦ 9 mm | Tabulae Biologicae |
|---|---|---|---|
| 1,33 | ≦ No | ≦ 1,34 | " |
| 0,5 mm | ≦ ec | ≦ 30 mm | |
| 1,3 | ≦ Nc | ≦ 2,0 | |
| 2 mm | ≦ Re | ≦ 100 mm | |
| 1,3 | ≦ Ne | ≦ 2,0 | |
| 0,5 mm | ≦ ee | ≦ 30 mm | |
| 0,5 mm | ≦ d | ≦ 30 mm | |

Rc can take any value.

The foregoing equations are valid for contact lenses formed by the coupling of just two lenses. Similar equations could be established in case either of those lenses, or even both, should in turn be formed by the coupling of elementary lenses. Such a construction would not depart from the scope of this invention. It is likewise clear that the contact lens could be formed only by a single lens in one piece. In that case, the coupling surface of the two lenses of the construction described above could be considered a fictitious surface separating the contact lens into two portions situated on both sides of that fictitious surface and having the same index. The foregoing equation is then converted simply by equalizing indices Nc and Ne and by cancelling magnitude ec and ec representing the total thickness of the lens.

The diagram of FIG. 1 relates to the case where the working point is placed in the very axis of the eye. As will be seen below, a number of diseases might require intervention in other regions of the eye. In that event, the contact lens will have to be kept on the cornea so that its optic axis 6 forms an angle α with the axis of the eye 10 (FIG. 2). Designating the distance of working point T from axis 10 by h and the depth of projection T' of point T on axis 10 by D, under these conditions, the following equations can be established:

$$h = -(Ro - D) \, tg \, \alpha$$

$$d = RO - \frac{Ro - D}{\cos \alpha}$$

For an operation such as an iridectomy, the value of D ranges between 3.4 mm and 4.2 mm (Tabulae Biologicae). The inclination can be chosen between 0° and 60°, depending on the position of point T.

By way of nonlimitative example of particular embodiments of the invention, two contact lens units made from contact lenses available on the market will be described below. Entry lenses dimensioned so that the contact lens units thus formed are in accordance with the invention were coupled with those lenses.

Thus, the contact lens 1 of FIG. 3 is particularly suitable for iridectomy with a view, for example, to the treatment of narrow-angle or vitreous-block glaucomas, for performation of the anterior capsule of the crystalline or even for the ablation of membranes in the anterior chamber of the eye. In the application represented on FIG. 3, working point T is on the iris 11 of the eye 3. The contact lens 5 is a lens available on the market under the name of HAAG-STREIT No. 902, from which the mirror it normally contains has been removed. The characteristics of that lens are as follows:

Nc=1.492; ec=13.2 mm; Rc=∞.

The exit or contact surface of that lens, which must be applied to the cornea, is concave and its radius of curvature is 7.4 mm.

Coupled on the plane face of that lens is a BK7 glass plano-convex entry lens 4 approximately 19 mm in diameter and the characteristics of which are as follows:

Ne=1.507; ee=6.1 mm; Re=∞.

As can be seen on the figure, the width of a treatment beam is brought by the air-entry lens diopter from a value of 16° to the value of 24°.

The entry surface 8 has been treated with anti-reflector for the wavelengths of the treatment beam (1.06μ) and for the visible radiation.

The inclination of the lens in relation to the axis 10 of the eye is in the order of 40° to 50°. The parameters of the entry lens have been calculated for the values 48° and D=3.6 mm.

The aberrations introduced by such a lens are limited to those created by the plane diopter between the two coupled lenses having a difference in index of only approximately 1% and the contact lens-cornea and cornea-aqueous humor spherical diopters. Under good working conditions, those aberrations remain very slight, notably, when the axis of the optical beam passes through the center of curvature of those diopters. In that connection, it is also to be noted that it will be in the interest of the user of the contact lens to respect as much as possible the theoretical conditions of orientation of the lens, but to maintain, nevertheless, a certain freedom of motion.

Figure 4:
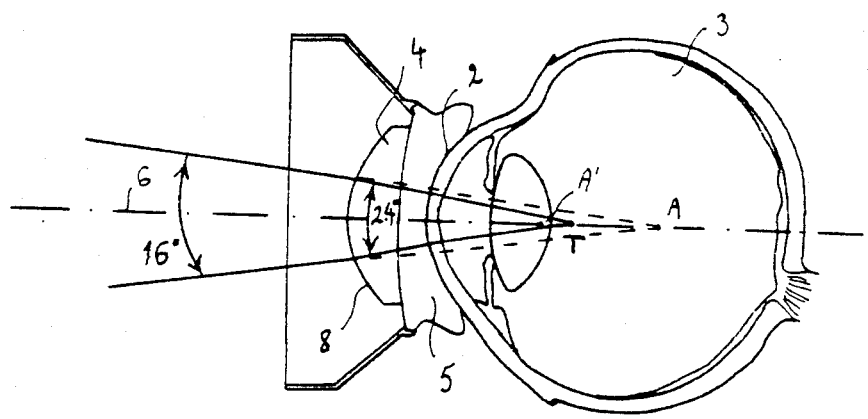

As far as the contact lens of FIG. 4 is concerned, it is particularly designed for interventions in the posterior region of the crystalline, e.g., for the ablation of membranes, perforation of the posterior capsule of the crystalline or destruction of the crystalline in the treatment of cataract.

Contact lens 5 is a lens available on the market under the name of HAAG-STREIT No. 901, containing an exit or contact surface designed to be applied to the concave cornea, with radius of curvature of 7.4 mm. The other parameters of that lens are:

Ne=1.492; ee=1.17 mm; Rc=150 mm.

Coupled with that contact lens 5 is a BK7 glass convergent mechanical type entry lens 4 having the following characteristics:

Ne=1.507; ee=3.65 mm; Re=8.01 mm; Rc=150 mm.

As can be seen on the figure, the configuration of the contact lens is such that working point T is situated between Weierstrass points A and A', at a distance d of 8.5 mm from the surface of the cornea. The aberrations created by that lens are extremely slight.

In general, the contact lenses according to the invention are characterized by a very great improvement in reliability of use, by comparison with previous devices. Thus, increase in the width of the treatment beam leads to a corresponding diminution of the focal spot, to an increase of the energy density at that point making it possible to diminish the energy of the beam necessary for optical click, and to a better localization of optical click, the stability of which will be better; that is, for different successive pulses it will always occur in the same places, which increases the effectiveness of treatment. Furthermore, the beam being wider, the energy capable of falling on the retina or the regions of the eye situated before or after the working point will always be less.

What is claimed is:

1. A contact lens for the observation and treatment by a coherent radiation beam of a working point in an eye, said contact lens comprising a symmetry axis, a spherical entry surface associated with Weierstrass points A and A' and a contact surface designed to be applied to the cornea of the eye, the optic centers of said entry and contact surfaces being situated on the symmetry axis of the lens, the radius of curvature of said entry surface being determined for the image of point A' by the rest of the contact lens and the parts of the eye crossed by the beam bringing the image of point A' to said working point, whereby said beam is focalized at said working point with minimal aberrations.

2. The contact lens of claim 1, comprising at least a first lens having said entry surface and a second lens coupled to said first lens and having said contact surface, the optic axes of said lenses being merged.

3. The contact lens of claim 2, wherein the radius of curvature of said entry surface is defined by the following equation:

$$Re \simeq \frac{Ne^2}{Ne+1} \left( \frac{1}{\frac{Nc}{\frac{No}{d} + \frac{Nc-No}{Ro}} + ec} + \frac{Ne-Nc}{Rc} + \frac{ee}{Ne} \right)$$

in which
Ne, Nc and No are the indices of refraction of the first lens, of the second lens and of the eye respectively;
Re is said radius of curvature of the entry surface;
Rc is the radius of curvature of a first diopter formed by the first and the second lens;
Ro is the radius of curvature of a second diopter formed by the second lens and the eye;
d is the distance between said working point and the second diopter in the axis of the contact lens; and
ee and ec are the distances between said entry surface and said first diopter and said first and second diopters respectively in the axis of the contact lens.

4. The contact lens of claim 3, wherein

| 7 mm | ≦ Ro | ≦ 9 mm |
|---|---|---|
| 1,33 | ≦ No | ≦ 1,34 |
| 0,5 mm | ≦ ec | ≦ 30 mm |
| 1,3 | ≦ Nc | ≦ 2,0 |
| 2 mm | ≦ Re | ≦ 100 mm |
| 1,3 | ≦ Ne | ≦ 2,0 |
| 0,5 mm | ≦ ee | ≦ 30 mm |
| 0,5 mm | ≦ d | ≦ 30 mm |

5. The contact lens of claim 2, wherein the first lens is made of mineral glass and the second lens is made of an organic material.

6. The contact lens of claim 5, wherein said entry surface is coated with an anti-reflector.

7. The contact lens of claim 5, wherein said second lens is a mirrorless HAAG-STREIT No. 902 type contact lens having a plane entry surface, a concave contact surface of 7.4 mm radius of curvature, a center thickness of 13.2 mm and an index of refraction of 1.492, and said first lens is a BK7 glass planoconcave lens having an index of refraction of 1.507 and a center thickness of approximately 6.1 mm and the entry surface of which has a radius of curvature of approximately 13.03 mm.

8. The contact lens of claim 7, wherein the diameter of the first lens is in the order of 19 mm.

9. The contact lens of claim 5, wherein said second lens is a HAAG-STREIT No. 901 type contact lens having a convex entry surface of 150 mm radius of curvature, a concave contact surface of 7.4 mm radius of curvature, a center thickness of 1.17 mm and an index of refraction of 1.492, and said first lens is a BK7 glass convergent meniscus type lens having an index of refraction of 1.507 and a center thickness of approximately 3.65 mm, of which the entry surface has a radius of curvature of approximately 8.01 mm and the exit surface a radius of curvature of approximately 150 mm.

10. The contact lens of claim 9, wherein the diameter of the entry lens is approximately 12 mm.

* * * * *